US008802036B2

(12) United States Patent
Chen et al.

(10) Patent No.: US 8,802,036 B2
(45) Date of Patent: *Aug. 12, 2014

(54) REACTION CASSETTE AND ASSAY DEVICE (71) Applicant: Apex Biotechnology Corp., Hsinchu (TW)

(72) Inventors: Sz-Hau Chen, Taipei (TW); Yueh-Hui Lin, Hsinchu (TW); Chun-Ju Chen, Taitung (TW)

(73) Assignee: Apex Biotechnology Corp., Hsinchu (TW)

( * ) Notice: Subject to any disclaimer, the term of this patent is extended or adjusted under 35 U.S.C. 154(b) by 0 days.

This patent is subject to a terminal disclaimer.

(21) Appl. No.: 13/668,301

(22) Filed: Nov. 4, 2012

(65) Prior Publication Data
US 2013/0121898 A1   May 16, 2013

Related U.S. Application Data

(63) Continuation-in-part of application No. 12/832,030, filed on Jul. 7, 2010, now Pat. No. 8,617,490.

(60) Provisional application No. 61/558,055, filed on Nov. 10, 2011.

(51) Int. Cl.
*G01N 15/06* (2006.01)

(52) U.S. Cl.
USPC ............ 422/554; 422/50; 422/68.1; 422/547; 422/550; 422/551

(58) Field of Classification Search
USPC .................. 422/554, 50, 68.1, 547, 550, 551
See application file for complete search history.

(56) References Cited

U.S. PATENT DOCUMENTS

2007/0004029 A1 *   1/2007   Aoyagi ..................... 435/287.2

FOREIGN PATENT DOCUMENTS

| JP | 03-046566 | 2/1991 |
| JP | 03-223674 | 10/1991 |
| JP | 2011-099852 | 5/2011 |

* cited by examiner

*Primary Examiner* — Sam P Siefke
(74) *Attorney, Agent, or Firm* — Liu & Liu (57) ABSTRACT

A reaction cassette for biochemical assay, a biochemical assay device including a first space configured to accommodate liquid, having a first opening and rounding edges, a direction of the first opening being directed upward. A second space includes a second opening, a direction of the second opening being perpendicular to the direction of the first opening, wherein the first space and the second space are disposed such that when the reaction cassette is rotated allowing the liquid to drain into the second space. A third space is located below the first space and having a third opening, a direction of the third opening being upward such that when the reaction cassette is reversibly rotated allowing the liquid to drain into the third space, wherein an array of bumps is disposed in the third space to create turbulence of the liquid. An inner partition wall, connected with the second opening and the third opening, acts as a liquid flow channel between the second space and the third space.

17 Claims, 12 Drawing Sheets

REACTION CASSETTE AND ASSAY DEVICE

CROSS REFERENCE TO RELATED APPLICATIONS

This application is a Continuation In Part (CIP) Application of U.S. application Ser. No. 12/832,030, filed on Jul. 7, 2010, which is incorporated herein by reference in its entirety. This application claims priority to U.S. provisional Application No. 61/558,055 entitled "REACTION CASSETTE, ASSAY DEVICE, AND ASSAY METHOD", filed on Nov. 10, 2011, which is incorporated herein by reference in its entirety for all purposes.

FIELD OF INVENTION

The present invention relates to an assay device and an assay method using the assay device, and more particularly, to a biochemical assay device for measuring characteristics of liquid sample and an assay method using the biochemical assay device.

BACKGROUND OF THE INVENTION

In vitro diagnostic (IVD) assay has been widely utilized in the qualitative and quantitative assessment of body fluid for providing information regarding diagnosis and therapy. For this reason, IVD assay has become an increasingly important means in medical industry.

Generally, the forgoing IVD assay techniques require the utilization of assay devices and measurement instruments, as well as the reagent preparation. During the assay procedure, the blood sample or other body fluid samples may need to be collected manually, so that the samples are more likely to be contaminated and risk of infection is highly increased.

Further, different reagents may need to be added sequentially to react with the sample during the assay operation. If these steps are executed by user's direct operation, the procedure may become complicated and take a long time. Besides, there is also a problem in that waste liquid treatment is required after the assay procedure.

Accordingly, there is a long-felt but unmet need to have an assay device and an assay method capable of overcoming limitations of the prior art, such that the measurement process and the waste liquid treatment can be performed easily and securely.

SUMMARY OF THE INVENTION

In view of the problems existing in the prior art, the present invention provides an assay device for measuring characteristics of liquid sample and an assay method using the assay device. The device and the method of the present invention can be used in various chemical assays, medical assays, or other similar assays having multiple steps of mixing reagents/reactants and sample.

In one embodiment, the biochemical assay device of the present invention can be used to facilitate the examination and analysis process having multiple reaction steps between liquid sample (e.g. blood sample) and reagent (or reactant). According to optical characteristics of the liquid sample after the reaction, the amount of one or more ingredients of the liquid sample can be determined.

According to an aspect of the present invention, a reaction cassette for biochemical assay comprises a first space configured to accommodate liquid. The first space has a first opening and rounding edges. The direction of the first opening is directed upward. A second space has a second opening. The direction of the second opening is perpendicular to the direction of the first opening, wherein the first space and the second space are disposed such that when the reaction cassette is rotated allowing the liquid to drain into the second space. A third space is located below the first space and having a third opening. The direction of the third opening is upward such that when the reaction cassette is reversibly rotated allowing the liquid to drain into the third space, wherein an array of bumps is disposed in the third space to create turbulence of the liquid. An inner partition wall is connected with the second opening and the third opening, acting as a liquid flow channel between the second space and the third space.

According to another aspect of the present invention, a biochemical assay device comprises a reaction cassette for biochemical assay, which includes a first space configured to accommodate liquid. The first space has a first opening and rounding edges. The direction of the first opening is directed upward. A second space has a second opening, and the direction of the second opening is perpendicular to the direction of the first opening, wherein the first space and the second space are disposed such that when the reaction cassette is rotated allowing the liquid to drain into the second space. A third space is located below the first space and the third space has a third opening. The direction of the third opening is upward such that when the reaction cassette is reversibly rotated allowing the liquid to drain into the third space, wherein an array of bumps is disposed in the third space to create turbulence of the liquid. A first inner partition wall is connected with the second opening and the third opening, acting as a liquid flow channel between the second space and the third space. A sampling part that is configured to be coupled to the reaction cassette comprises a sampling tube, which is configured to draw a liquid sample, an absorption compartment containing an absorption material inside thereof, and a reservoir configured to store a liquid reagent.

The other aspects of the present invention, part of them will be described in the following description, part of them will be apparent from description, or can be known from the execution of the present invention. The aspects of the invention will be realized and attained by means of the elements and combinations particularly pointed out in the appended claims. It is to be understood that both the foregoing general description and the following detailed description are exemplary and explanatory only and are not restrictive of the invention, as claimed.

BRIEF DESCRIPTION OF THE PICTURES

The foregoing aspects and many of the attendant advantages of this invention will become more readily appreciated as the same becomes better understood by reference to the following detailed description, when taken in conjunction with the accompanying pictures, wherein.

DETAILED DESCRIPTION OF THE INVENTION

The present invention discloses an assay device and an assay method using the same for carrying out the process of analyzing constituents of a liquid sample in a more convenient and safer manner. The present invention will be described more fully hereinafter with reference to the FIGS. 1A-5F. However, it should be noted that the features illustrated in the drawings are not necessarily drawn to scale, and like reference numerals represent the same or similar elements. The devices, elements, and methods in the following description are configured to illustrate the present invention, and should not be construed in a limiting sense.

Figure 1A:
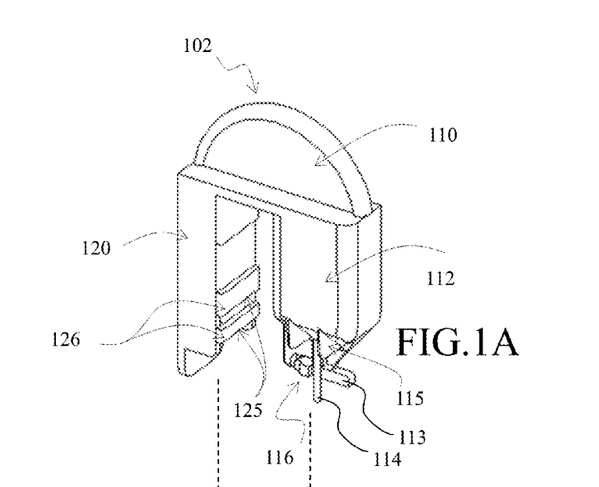
FIGS. 1A-1C illustrate a perspective exploded views of a biochemical assay device according to an embodiment of the present invention.
Figure 1B:
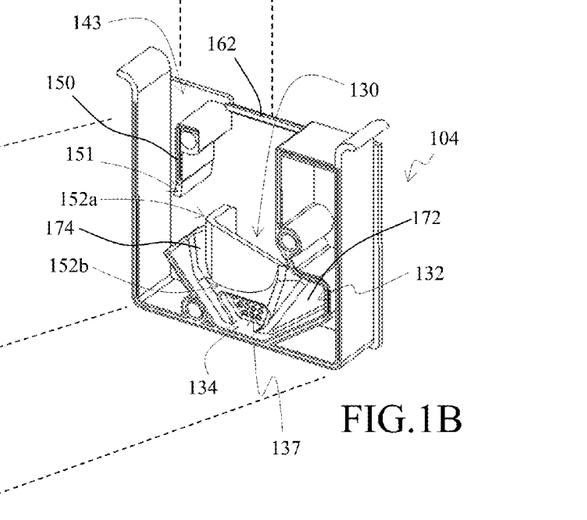
Figure 1C:
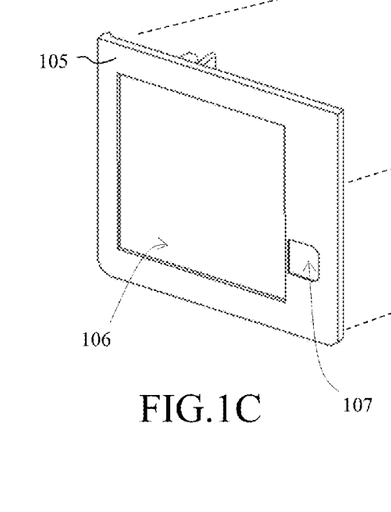

FIGS. 1A-1C illustrate perspective exploded views of a biochemical assay device 100 according to an embodiment of the present invention, which includes a sampling part 102, a reaction cassette base 104 and a cover 105 sealed with the reaction cassette base. The biochemical assay device 100 is preferably made of optical grade plastics formed by mold injection. In order to eliminate interference from lateral light, the surface of the reaction cassette is roughened and hazed. Small trenches or groove lines (141 also referring to FIG. 2) are formed atop the walls of reaction cassette base 104 yielding close bond after supersonically assembling the reaction cassette base 104 and cover 105. Furthermore, a bar code tag 106 is attached on the hazel surface of the cover 105. After the biochemical assay device is inserted in a measurement device that performs the assay procedure through an optical measurement region 107, the measurement device can detect built-in parameters stored in the bar code tag 106. In addition, the bar code tag 106 can be encrypted or unencrypted.

The sampling part 102, such as a sampling cartridge includes a reservoir 112 configured to store liquid reagents of various types, and an absorption compartment 120 containing an absorption material. Bumps 126 are disposed on one lateral side of the absorption compartment 120 configured with a latch 151 of the reaction cassette. The latch 151 can fix and stabilize during insertion of the sampling part, thereby preventing it from being reused and reducing some contamination and mismeasurement problems. In addition, tilt-guiding planes 125 are formed on the bumps 126 to improve smoothness during assembling.

The sampling tube 114 is configured to draw a liquid sample (such as blood sample). Preferably, the liquid sample is drawn by capillarity into the sampling tube 114. Liquid reagent can be sealed inside the reservoir 112 by a piece of aluminum foil (not shown in FIG. 1A; see FIG. 3B, element 316). A bump 116 is disposed on a transverse beam 113 adjacent to the sampling tube 114. During the insertion of the sampling part 102 into the reaction cassette 104, the foregoing aluminum foil can be removed automatically by rubbing and scraping against the reaction cassette 104. The bump 116 acted as a barb sticks to the upper rim 162 of back wall the cassette 104 and breaks with the transverse beam 113 while peeling off the aluminum foil. With the assistance of the bump 116 and the transverse beam 113, the aluminum foil can be evenly and smoothly peeled off eliminating vacuum effect and residue of liquid reagent.

Referring to FIG. 1B, in the inner space, the reaction cassette 104 includes an inner partition wall 150, defining an absorption space 143. The reaction cassette 104 further includes a first space 130, a second space 132, and a third space 134. Each of the first space 130, the second space 132, and the third space 134 has a function of accommodating liquid reagent. A first slant plane 172 is disposed between the second space 132 and the third space 134 such that the liquid is allowed to flow in smoothly. A second slant plane 174 is disposed between the third space and the absorption compartment such that the liquid is allowed to flow in smoothly. A first curved wall 152a and a second curved wall 152b are formed so as to create rounding edges in the first space. The first space with rounding edges can provide a channel for liquid reagent smoothly drained from the first space to the second space. An array of bumps 131 is disposed in the third space. After the liquid reagent drains to the third space, the flow creates turbulence due to impedance of the bumps 131, thereby enhancing reaction rate among the reagent and improving the measurement accuracy.

Figure 2:
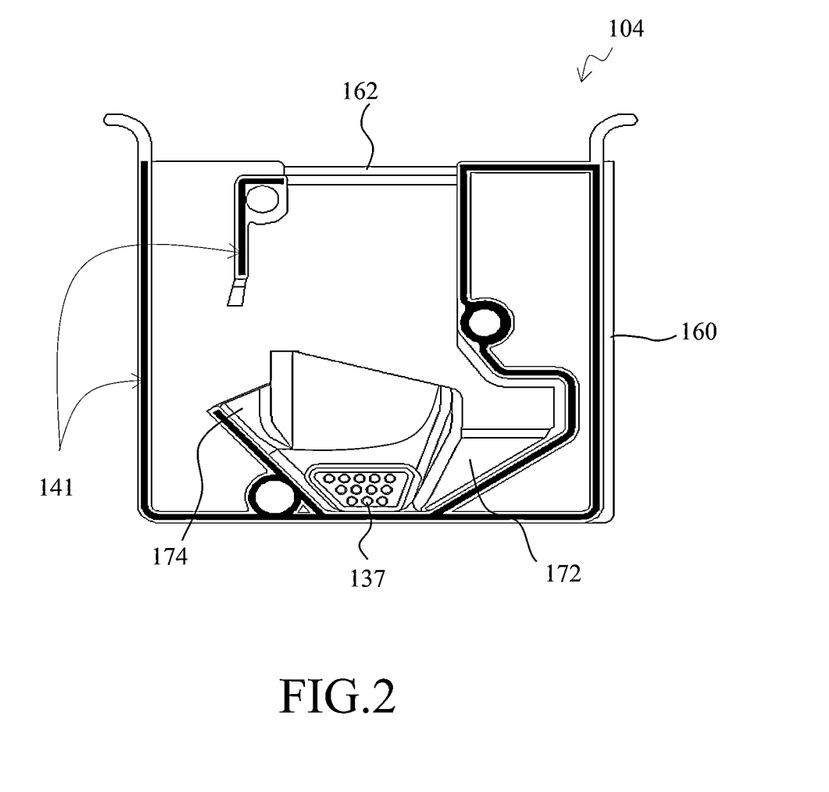
FIG. 2 shows a plan view of a reaction cassette illustrating supersonic microgrooves according to an embodiment of the present invention.

FIG. 2 shows a plan view of a reaction cassette illustrating supersonic microgrooves according to an embodiment of the present invention. Small trenches or groove lines 141 are formed atop the walls of the reaction cassette base. The cover and the reaction cassette base are bonded together by supersonic sealing. Instant heat is generated on contact areas due to supersonic waves resulting in a well-bonded reaction cassette.

Figure 3A:
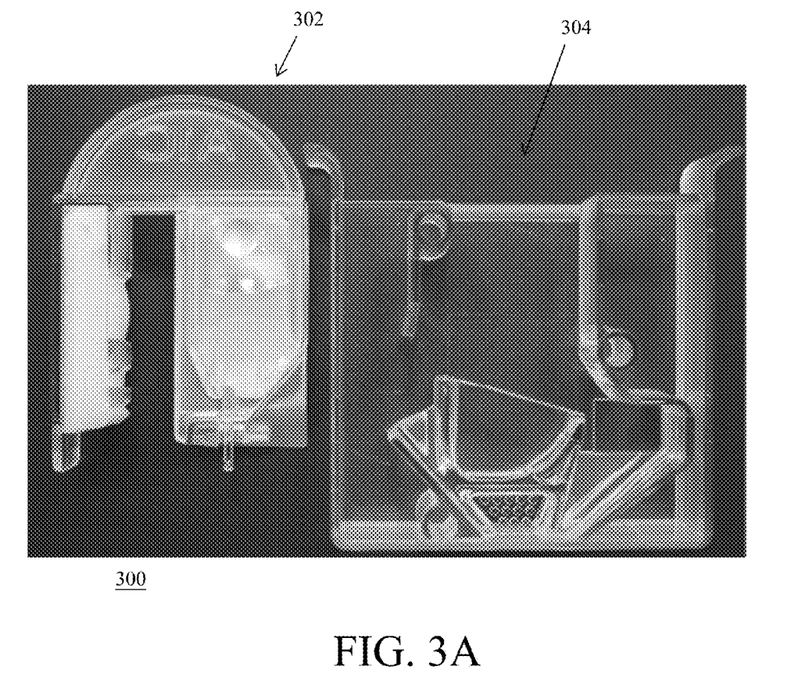
FIGS. 3A and 3B are respectively a front view photo and a back view photo of a biochemical assay device in accordance with one embodiment of the present invention.
Figure 3B:
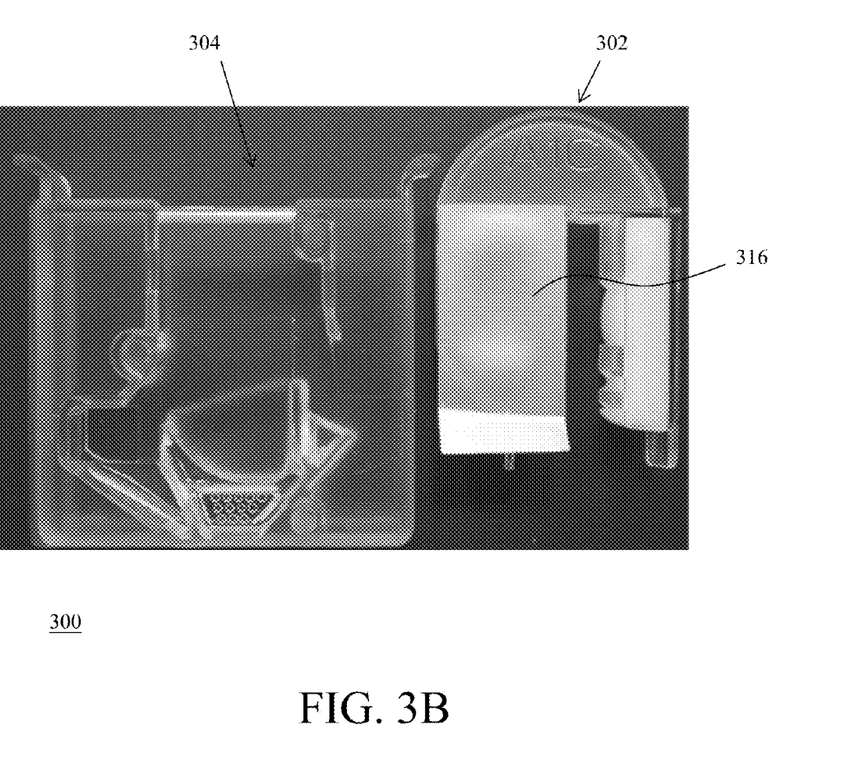

FIGS. 3A and 3B are respectively a front view photo and a back view photo of a biochemical assay device 300 in accordance with one embodiment of the present invention. In this embodiment, the biochemical assay device 300 includes a sampling part 302 and a reaction cassette 304 both made of transparent material, and the sampling part 302 further includes an aluminum foil 316 for providing a fluid-tight seal.

Figure 4A:
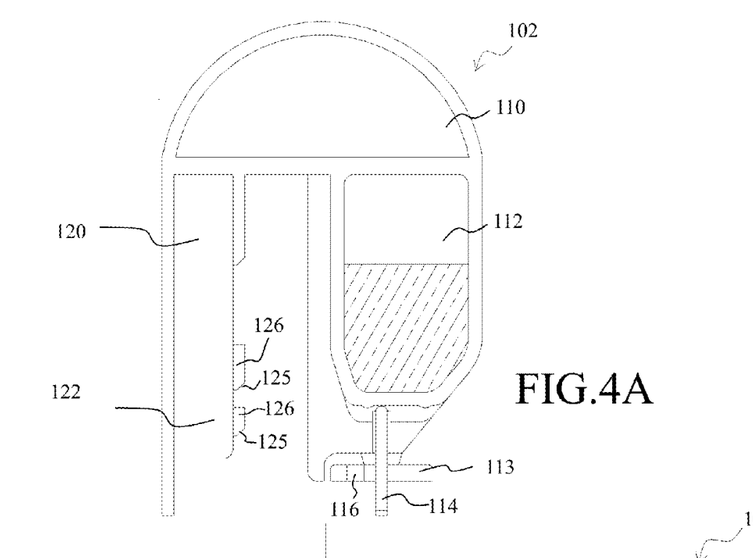
FIGS. 4A and 4B illustrate perspective views of a biochemical assay device according to an embodiment of the present invention.
Figure 4B:
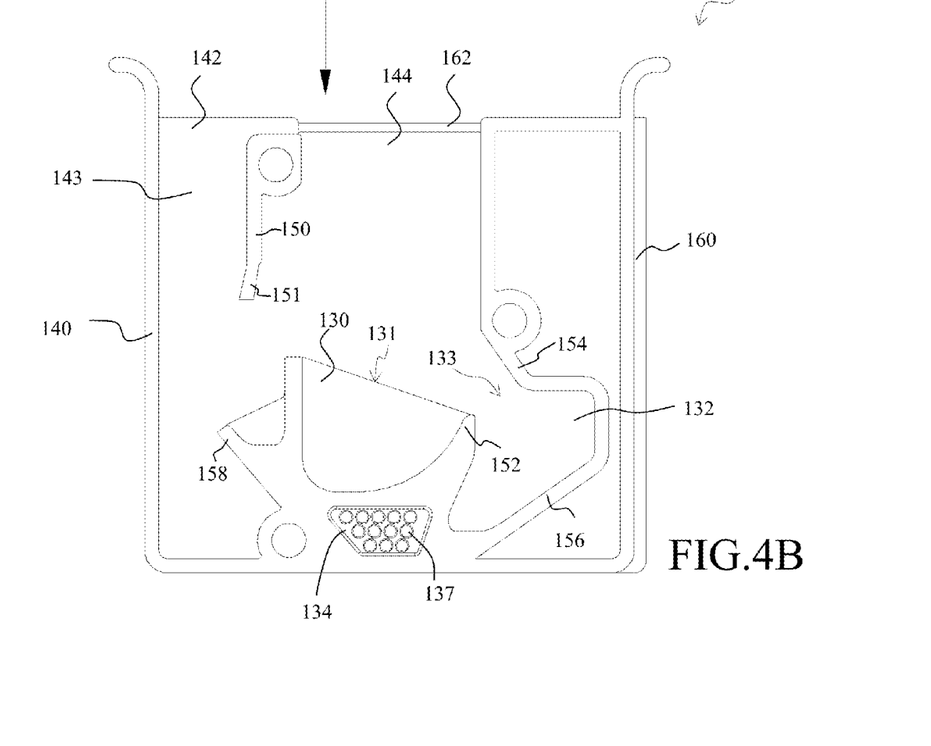

FIGS. 4A and 4B illustrate perspective views of a biochemical assay device 100 according to an embodiment of the present invention, which includes a sampling part 102 and a reaction cassette 104. The sampling part 102 includes a sampling tube 114, a reservoir 112 configured to store liquid reagents of various types, and an absorption compartment 120 containing an absorption material 122. The absorption compartment 120 is a hollow cylinder with an opening. The opening of the absorption compartment 120 can be arranged in the bottom of the absorption compartment 120 for facilitating extraction and insertion of the absorption material 122. The absorption material 122 can be any material of high absorptivity, such as cotton, sponge, filter paper, etc.

Figure 4C:
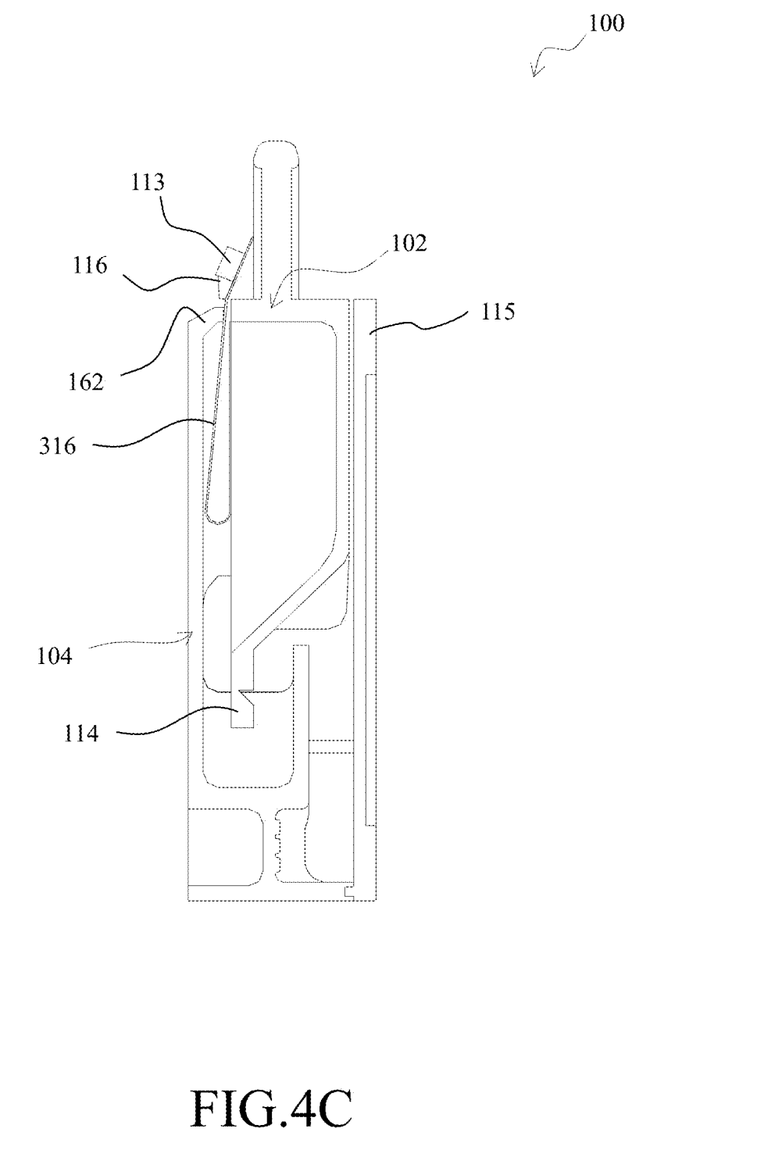
FIG. 4C shows a side view of the assembled biochemical assay device.

The sampling tube 114 is configured to draw a liquid sample (such as blood sample). Preferably, the liquid sample is drawn by capillarity into the sampling tube 114. In the embodiment that the liquid sample is a blood sample, the type of the liquid reagent stored in the reservoir 112 may vary depending on what ingredient in the blood sample is being tested (such as glucose, cholesterol, virus, etc.). For example, the liquid reagent can be antibody solution or reacting enzyme solution. The liquid reagent can be sealed inside the reservoir 112 by a piece of aluminum foil (not shown). It should be understand that the foregoing aluminum foil can be replaced by other flexible material which has deformable properties and liquid sealing function, such as plastic film and water-proof paper, etc. A bump 116 with one end attached to the aluminum foil is disposed on a transverse beam 113 adjacent to the sampling tube 114. FIG. 4C shows a side view of the assembled biochemical assay device. During the insertion of the sampling part 102 into the reaction cassette 104, the foregoing aluminum foil can be removed automatically by rubbing and scraping against the reaction cassette 104. The bump 116 acts as a barb to peel off the aluminum foil while the sampling part and the reaction cassette are assembled. The bump 116, together with the transverse beam 113, sticks to the upper rim 162 of back wall the cassette 104 while peeling off the aluminum foil. The assembling procedure of the sampling part 102 and the reaction cassette 104 should be taken enough care to avoid cross-contamination during the specimen handling steps.

Further, the sampling part 102 can include a hand holder 110 for allowing a user to easily manipulate the sampling part 102. Although, as shown in FIG. 4A, the hand holder 110 is preferably formed arc shape, other shapes can also be applied as long as the user can easily hold and operate the sampling part 102.

Referring to FIG. 4B, the reaction cassette 104 includes an outer wall 140 defining an inner space and having two inlets 142 and 144 leading into the inner space. In the inner space, the reaction cassette 104 further includes an inner wall 150, an inner wall 152, and inner wall 154, an inner wall 156, an inner wall 158, a first space 130, a second space 132, and a third space 134. Each of the first space 130, the second space 132, and the third space 134 has a capability of accommodating liquid.

The first space 130 has a first opening 131 and the second space 132 has a second opening 133. The first opening 131 faces upward, i.e. the direction of the first opening 131 is vertically upward, while the direction of the second opening 133 is perpendicular to the direction of the first opening 131. The first space 130 and the second space 132 are disposed such that when the reaction cassette 104 is rotated, liquid in the first space 130 can flow into the second space 132. In the embodiment shown in FIG. 4A, by rotating the reaction cassette 104 clockwise, the liquid in the first space 130 can flow into the second space 132 through the inner wall 152 under the influence of gravity. The inner wall 154, being extended from the second space 132, is configured to prevent the liquid from leaking out of a desired flow path during the time that the liquid flows from the first space 130 into the second space 132. The third space 134 is located below the first space 130 and has a third opening 135 whose direction is the same as the direction of the first space 130. The inner wall 156, being connected to both of the second opening 133 and the third opening 135, functions as a liquid flow channel between the second space 132 and the third space 134.

As shown in FIGS. 4A and 4B, the inner wall 150 is located below both of the inlet 142 and the inlet 144 for guiding the sampling part 102 inserted into the reaction cassette 104. It should be noted that the position and the angle of the inner wall 150 can vary depending on the structure of the sampling part 102. Furthermore, the inner wall 158, being connected to the third opening 135, can function as a liquid flow channel between the third space 134 and the absorption compartment 120 when the sampling part 102 is inserted into the reaction cassette 104.

The aluminum foil enclosing the back of the sampling part 102 can be readily and easily removed when the sampling part 102 is inserted into the reaction cassette 104, such that the liquid reagent stored in the reservoir 112 and the liquid sample contained in the sampling tube 114 can flow into the first space 130. After the liquid reagent and the liquid sample are mixed and react with each other in the first space 130, the reaction cassette 104 can be rotated to allow the mixture of the liquid reagent and the liquid sample to flow from the first space 130 into the second space 132 under the force of the gravity. Subsequently, an optical measurement (such as optical density (O.D.) measurement) can be performed with respect to the mixture in the second space 132 to determine the characteristics of the mixture. Subsequently, the reaction cassette 104 is rotated to move the mixture of the liquid reagent and the liquid sample through the inner wall 156 into the third space 134 by virtue of the gravity. The inner surface of the third space 134 is coated with a layer of reactant material (such as antibody or enzyme) in advance, such that the liquid sample, liquid reagent, and reactant material can mixed and react with each other in the third space 134. Next, the reaction cassette 104 is rotated again to move the mixture of the liquid sample, liquid reagent, and reactant material through the inner wall 156 into the second space 132, and then a second optical measurement is performed thereon. After the optical measurement is completed, the reaction cassette 104 is rotated to move the mixture through the inner walls 156 and 158 into the absorption compartment 120 of the sampling part 102 to be absorbed by the absorption material 122. Finally, the waste liquid can be easily removed from the reaction cassette 104 by drawing out the absorption material 122.

After being combined with the sampling part 102, the reaction cassette 104 can be put into a measurement instrument (not shown). The measurement instrument can rotate the reaction cassette 104 clockwise or counterclockwise according to a predetermined rule, such that the liquid sample, liquid reagent, and reactant material can mix and react with each other in sequence. Correspondingly, the reaction cassette 104 can further include an error-proof 160 for preventing the reaction cassette 104 from being placed into the measurement instrument in wrong directions. In one embodiment, the error-proof 160 is a protrusion connected to the outer wall 140.

The reaction cassette 104 can be made of glass, resin, or other transparent materials by a method well known in the art, such as injection-molding technique. In one embodiment, the reaction cassette 104 is implemented by an integral forming technique.

Figure 5A:
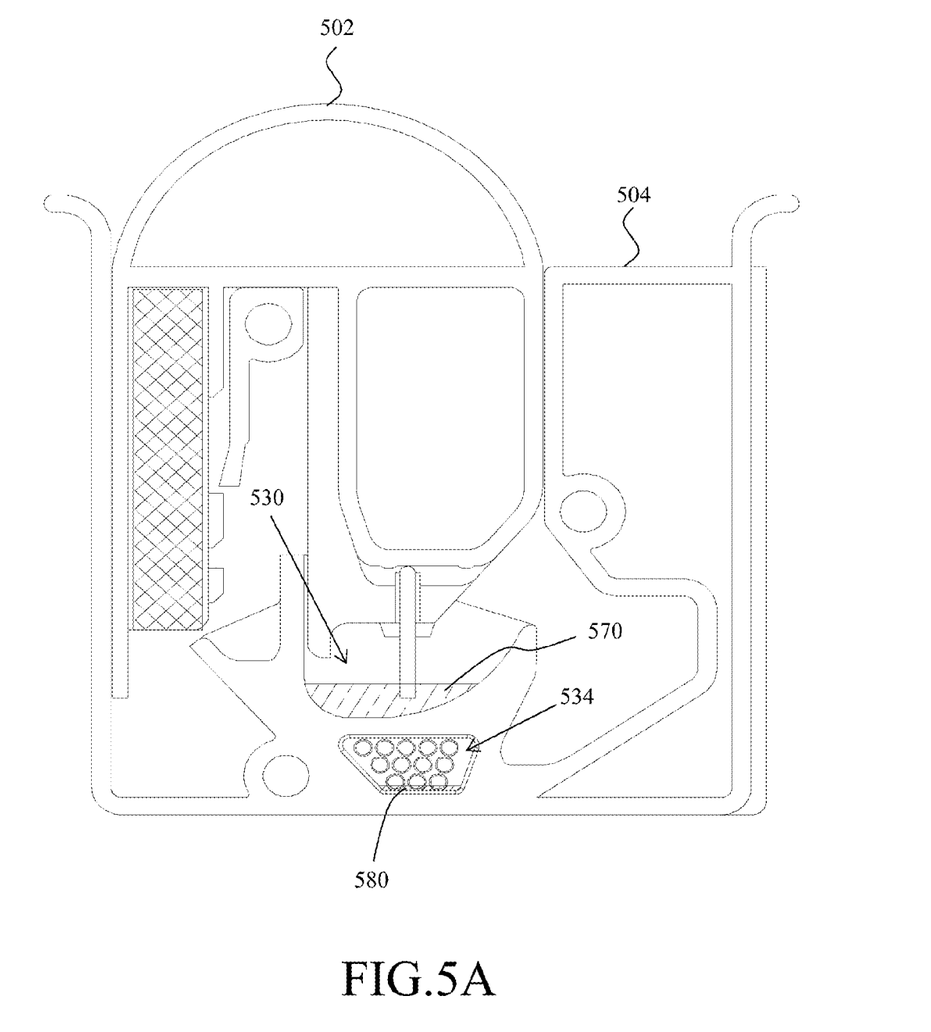
FIGS. 5A-5F are illustrative diagrams showing steps of the biochemical assay method.

FIGS. 5A-5F are illustrative diagrams showing steps of the biochemical assay method. Adequate mixing is necessary to achieve accurate assay results. Referring to FIG. 5A, the liquid reagent is stored in the sampling part 502, the liquid sample is drawn by the sampling part 502, and the reactant material 580 is applied to the surface of the third space 534 of the reaction cassette 504. The sampling part 502 is inserted into the reaction cassette 504, so that the liquid reagent and the liquid sample in the sampling part 502 can flow into the first space 530 of the reaction cassette 504 in the direction indicated by the arrow shown in FIG. 5A. The liquid reagent and the liquid sample can be mixed more evenly by oscillating the reaction cassette 504, which then react with each other to form a first liquid mixture 570. Typically, the reactant material 580 is a film having substantially no fluidity under ordinary conditions, and therefore does not flow during the rotation of the reaction cassette 504. In one embodiment, the reactant material 580 can be formed on the surface of the third space 534 by the known coating or spraying method.

Figure 5B:
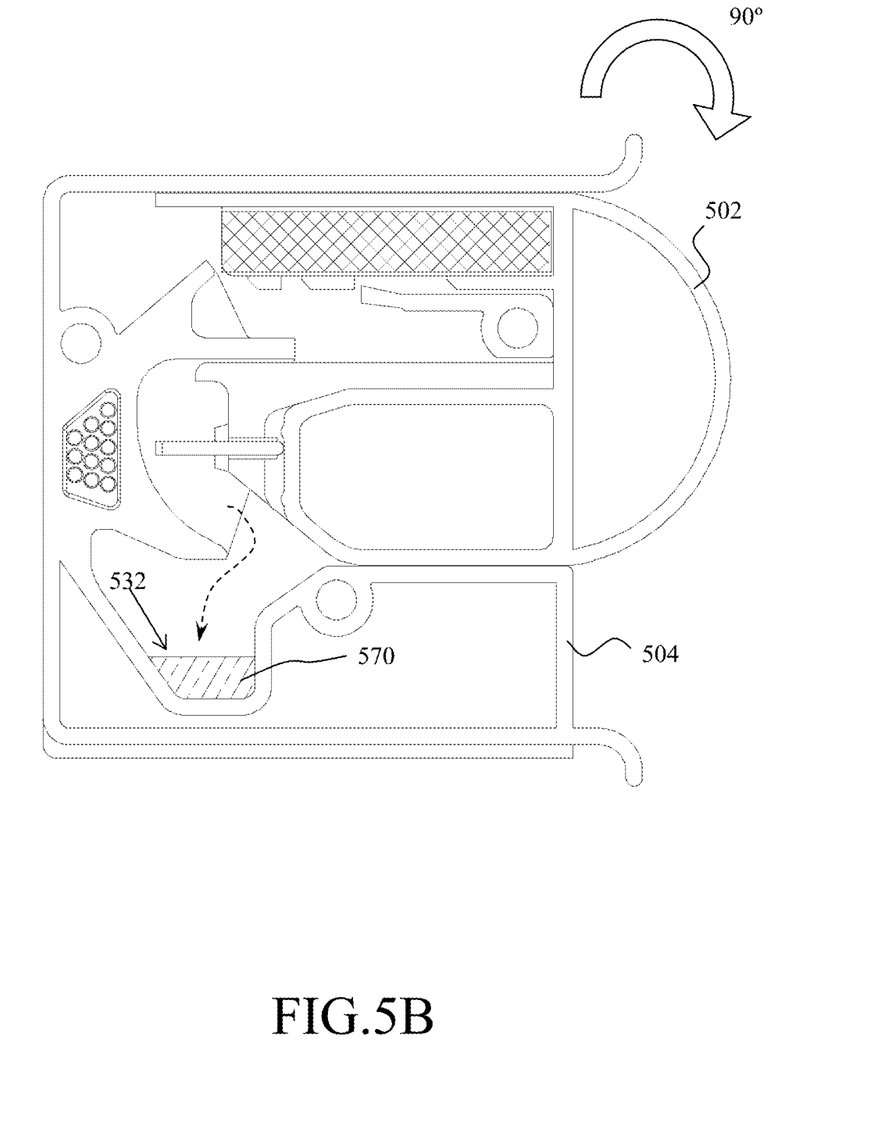
Figure 5C:
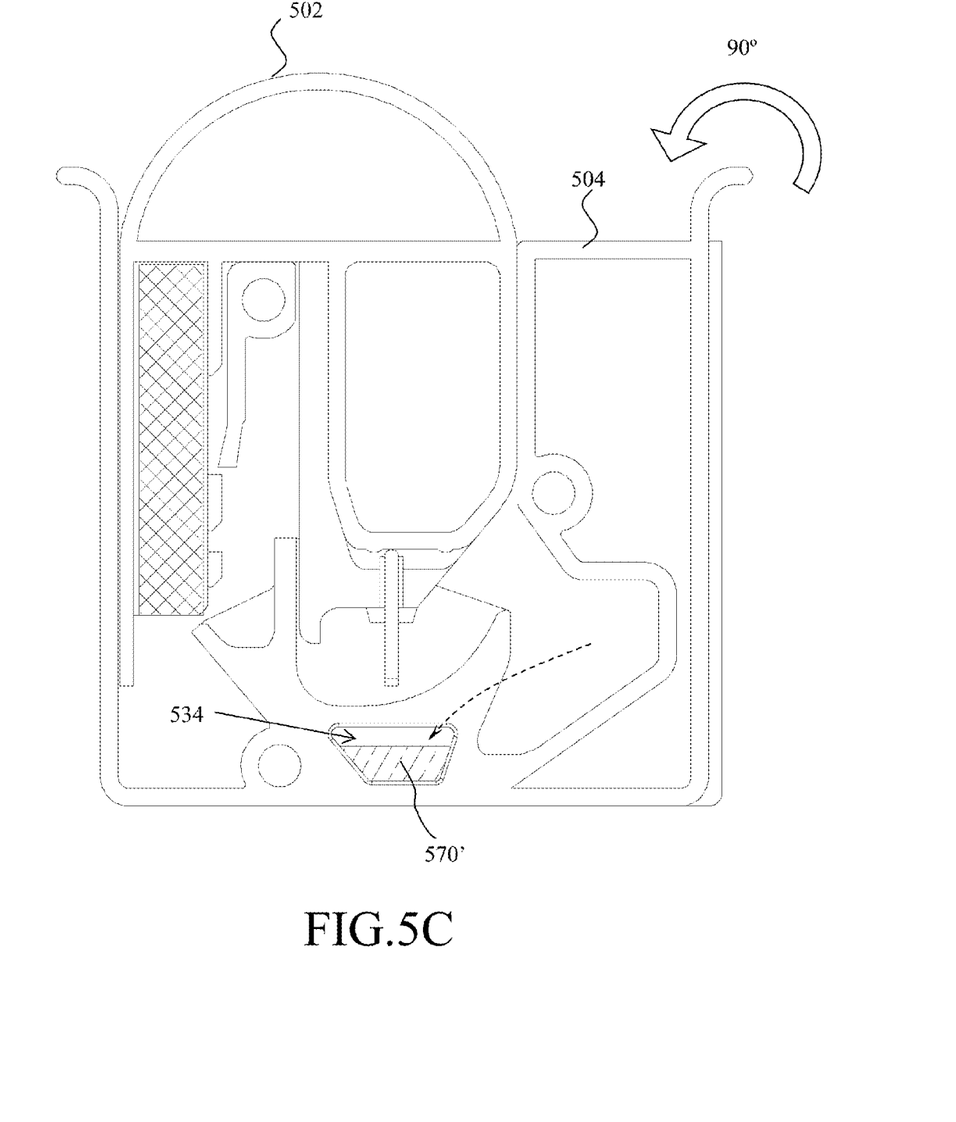
Figure 5D:
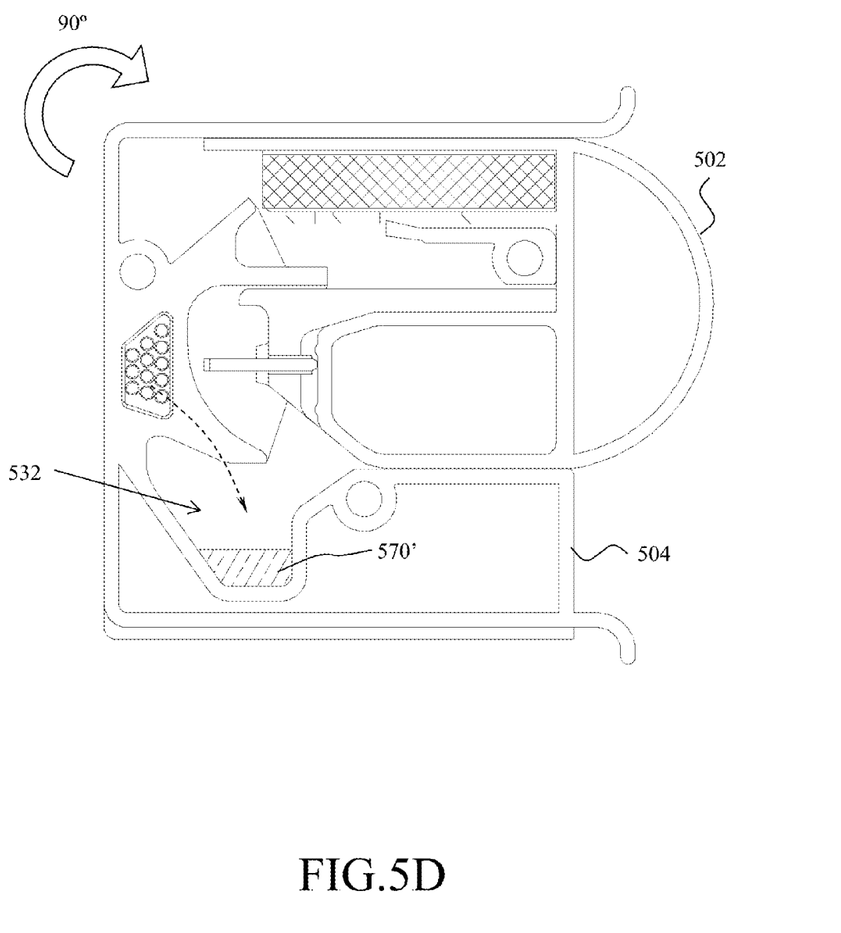

Next, referring to FIG. 5B, the reaction cassette 504 is rotated clockwise, whereby the first liquid mixture 570 can flow into the second space 532 of the reaction cassette 504 in the direction indicated by the arrow shown in FIG. 5B. In one embodiment, a rotation angle is preferably, but not limited to, about 70 degrees to about 110 degrees, and is more preferably about 90 degrees. Next, an optical measurement is performed with respect to the first liquid mixture 570 in the second space 532. In one embodiment, measurement of the optical density of the first liquid mixture 570 in the second space 532 is preferably performed by using a light having wavelength of 660 nm. Next, referring to FIG. 5C, the reaction cassette 504 is rotated counterclockwise, whereby the first liquid mixture 570 can flow into the third space 534 of the reaction cassette 504 in the direction indicated by the arrow shown in FIG. 5C. In one embodiment, a rotation angle is preferably, but not limited to, about 70 degrees to about 110 degrees, and is more preferably about 90 degrees.

Next, the first liquid mixture 570 can be mixed with the reactant material 580 in the third space 534 more evenly by oscillating the reaction cassette 504, which then react with each other to form a second liquid mixture 570'. Next, referring to FIG. 5D, the reaction cassette 504 is rotated clockwise, whereby the second liquid mixture 570' consisted of the liquid reagent, the liquid sample, and the reactant material can flow into the second space 532 of the reaction cassette 504. In one embodiment, a rotation angle is preferably, but not limited to, about 70 degrees to about 110 degrees, and is more preferably about 90 degrees. Next, an optical measurement is performed with respect to the second liquid mixture 570' in the second space 532. In one embodiment, is performed to measure the optical density of the second liquid mixture 570' in the second space 532 by using a light having wavelength of 660 nm. The optical signals measured can be converted into the electrical signals for subsequent analysis and comparison, so as to determine a ratio or a concentration of a specific ingredient in the liquid sample. Since both the optical measurements are performed in the second space 532, the measurement deviation caused by variations in the transparency or transmittance of the material of the reaction cassette 504 can be cancelled out.

Figure 5E:
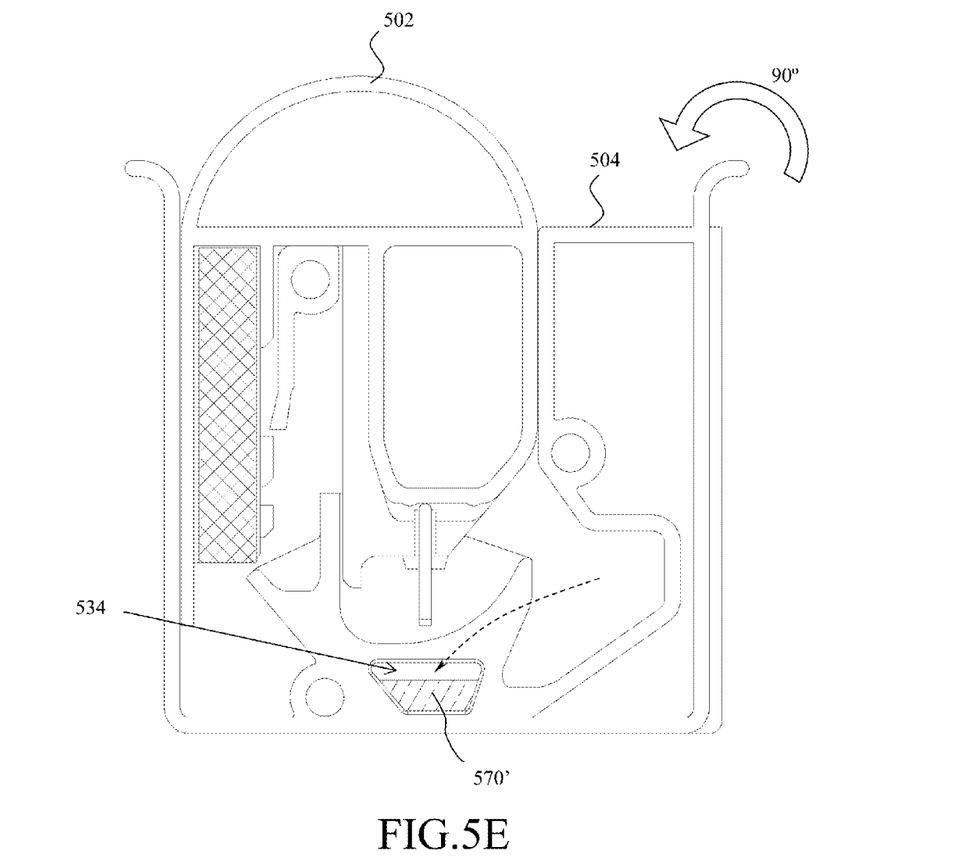
Figure 5F:
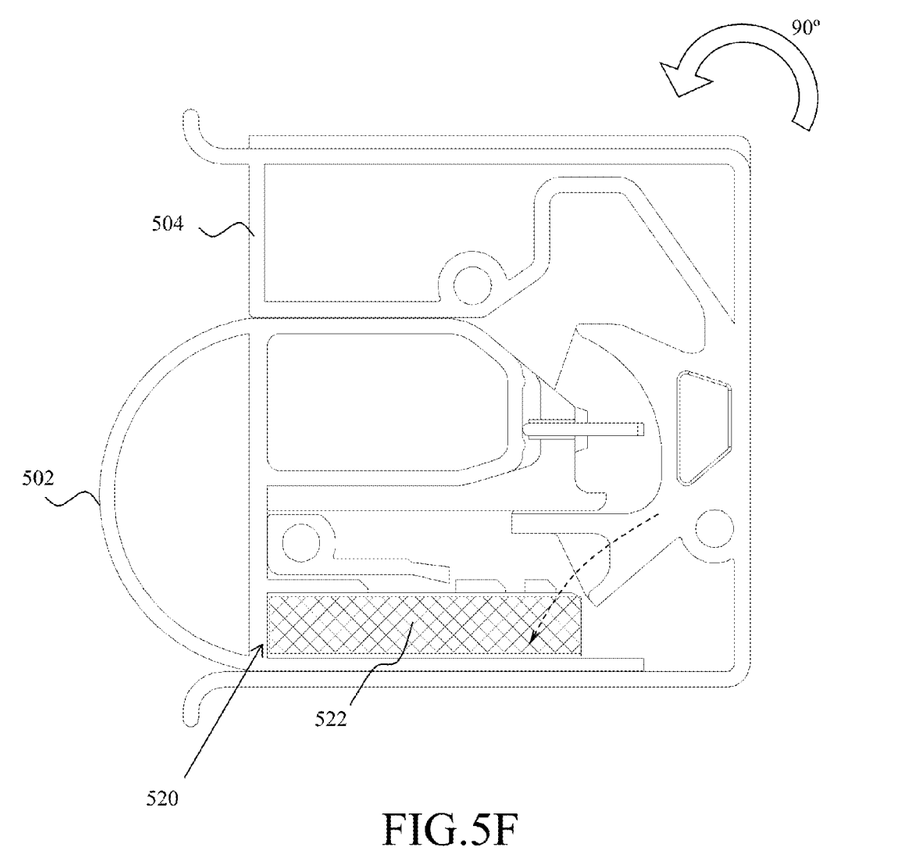

Subsequently, referring to FIGS. 5E and 5F, the reaction cassette 504 is rotated counterclockwise, whereby the second liquid mixture 570' can flow into the third space 534 and then into the absorption compartment 520 of the sampling part 502. Therefore, the second liquid mixture 570' can be absorbed by the absorption material 522 of the absorption compartment 520, so as to prevent environmental pollution and harm to human bodies caused by escaping waste liquid. In one embodiment, a rotation angle is preferably, but not limited to, about 160 degrees to about 200 degrees, and is more preferably about 180 degrees.

During the measurement process, the rotation of reaction cassette 504 can be performed automatically by a measurement instrument (not shown) according to a predetermined rule, such that the liquid sample, liquid reagent, and reactant material can be moved from one space to another space in the reaction cassette 504 in a desired sequence for carrying out the reaction and measurement steps. Therefore, user's operation load can be reduced through the method shown in FIGS. 5A-5F, for example, the user's manipulation of adding reagents to the liquid sample is not needed. On the other hand, since the rotation angle in each step can be about 90 degrees and about 180 degrees, which allows easy operation, the rotation steps of the assay method can be done manually and readily even when the measurement instrument is not available. Further, the waste liquid remaining after the assay procedure can be easily collected and handled by rotating the reaction cassette 504. To sum up, the assay device and the assay method disclosed in the present specification can increase user convenience, reduce man-made errors, and provide an easy and secure way for treatment of waste liquid.

The above illustration is for preferred embodiments of the present invention, is not limited to the claims of the present invention. Equivalent amendments and modifications without departing from the spirit of the invention should be included in the scope of the following claims.

The invention claimed is:

1. A reaction cassette for biochemical assay, comprising:
   a first space configured to accommodate liquid, having a first opening and rounding edges, a direction of the first opening being directed upward;
   a second space having a second opening, a direction of the second opening being perpendicular to the direction of the first opening, wherein the first space and the second space are disposed such that when the reaction cassette is rotated allowing the liquid to drain into the second space;
   a third space located below the first space and having a third opening, a direction of the third opening being upward such that when the reaction cassette is reversibly rotated allowing the liquid to drain into the third space, wherein an array of bumps is disposed in the third space to create turbulence of the liquid; and
   an inner partition wall, connected with the second opening and the third opening, acting as a liquid flow channel between the second space and the third space.

2. The reaction cassette according to claim 1, wherein the reaction cassette is made of optical grade transparent material.

3. The reaction cassette according to claim 1, wherein a slant plane is disposed between the second space and the third space such that the liquid is allowed to flow in smoothly.

4. The reaction cassette according to claim 1, further comprising an outer wall defining an inner space, wherein the first space, the second space, the third space, and the inner partition wall are disposed within the inner space, and the outer wall comprising an inlet located above the first space.

5. The reaction cassette according to claim 3, further comprising a protrusion connecting with the outer wall for preventing the reaction cassette from being placed into a measurement instrument in wrong directions.

6. The reaction cassette according to claim 1, further comprising a cover sealed on the outer wall and inner partition walls by supersonic sealing.

7. A biochemical assay device, comprising:
   a reaction cassette for biochemical assay, comprising:
   a first space configured to accommodate liquid, having a first opening and rounding edges, a direction of the first opening being directed upward;
   a second space having a second opening, a direction of the second opening being perpendicular to the direction of the first opening, wherein the first space and the second space are disposed such that when the reaction cassette is rotated allowing the liquid to drain into the second space;
   a third space located below the first space and having a third opening, a direction of the third opening being upward such that when the reaction cassette is reversibly rotated allowing the liquid to drain into the third space, wherein an array of bumps is disposed in the third space to create turbulence of the liquid; and
   a first inner partition wall, connected with the second opening and the third opening, acting as a liquid flow channel between the second space and the third space; and
   a sampling part configured to be coupled to the reaction cassette, comprising:
   a sampling tube configured to draw a liquid sample;
   an absorption compartment containing an absorption material inside thereof; and
   a reservoir configured to store a liquid reagent.

8. The biochemical assay device according to claim 7, wherein the reaction cassette is made of optical grade transparent material.

9. The biochemical assay device according to claim 7, wherein a first slant plane is disposed between the second space and the third space such that the liquid is allowed to flow in smoothly.

10. The biochemical assay device according to claim 9, wherein a second slant plane is disposed between the third space and the absorption compartment such that the liquid is allowed to flow in smoothly.

11. The biochemical assay device according to claim 7, further comprising an outer wall defining an inner space, wherein the first space, the second space, the third space, and the inner partition wall are disposed within the inner space, and the outer wall comprising an inlet located above the first space.

12. The biochemical assay device according to claim 11, further comprising a protrusion connecting with the outer wall for preventing the reaction cassette from being placed into a measurement instrument in wrong directions.

13. The biochemical assay device according to claim 7, wherein the sampling part is inserted into the reaction cassette through inlets, and the reaction cassette further comprises:
   a second inner partition wall, connected with the third space, acting as a liquid flow channel between the third space and the absorption compartment; and
   a third inner partition wall disposed to separate two sub-inlets to guide the sampling cartage into the reaction cassette.

14. The biochemical assay device according to claim 7, wherein the sampling part includes a pair of bumps on a surface of the absorption compartment and the third inner partition wall include an extended end stuck between the pair of bumps while the sampling part and the reaction cassette are assembled.

15. The biochemical assay device according to claim 14, further comprising guiding parts are disposed on the reservoir facilitating the sampling tube which is in align with the first space while the sampling part and the reaction cassette are assembled.

16. The biochemical assay device according to claim 7, wherein the reservoir of the sampling part is sealed with an aluminum foil, and the aluminum foil is removed during insertion of the sampling part into the reaction cassette.

17. The biochemical assay device according to claim 13, further comprising a bump disposed on a transverse beam beside the sampling tube acted as a barb to peel off the aluminum foil while the sampling part and the reaction cassette are assembled.

* * * * *